United States Patent
Götz et al.

(10) Patent No.: US 11,338,001 B2
(45) Date of Patent: *May 24, 2022

(54) PROBIOTICS FOR AGGREGATION WITH DISEASE-ASSOCIATED SPECIES IN THE ORAL CAVITY

(71) Applicants: SYMRISE AG, Holzminden (DE); PROBI AB, Lund (SE)

(72) Inventors: Marcus Rudolf Götz, Oberweser (DE); Kerstin Holmgren, Helsingborg (SE); Niklas Larsson, Lund (SE); Bernd Fiebich, Freiburg (DE); William Wade, Clevedon (GB)

(73) Assignees: SYMRISE AG, Holzminden (DE); PROBI AB, Lund (SE)

( * ) Notice: Subject to any disclaimer, the term of this patent is extended or adjusted under 35 U.S.C. 154(b) by 35 days.

This patent is subject to a terminal disclaimer.

(21) Appl. No.: 16/478,514

(22) PCT Filed: Jan. 17, 2018

(86) PCT No.: PCT/EP2018/051112
§ 371 (c)(1),
(2) Date: Jul. 17, 2019

(87) PCT Pub. No.: WO2018/134256
PCT Pub. Date: Jul. 26, 2018

(65) Prior Publication Data
US 2019/0365833 A1    Dec. 5, 2019

(30) Foreign Application Priority Data
Jan. 18, 2017 (EP) .................. 17152068

(51) Int. Cl.
*A61K 35/747* (2015.01)
*A61K 9/00* (2006.01)

(52) U.S. Cl.
CPC .......... *A61K 35/747* (2013.01); *A61K 9/0053* (2013.01)

(58) Field of Classification Search
CPC ...... A61K 35/74; A61K 45/06; A61K 35/742; A61K 35/747; A61K 9/0053; A61K 2300/00; A61K 35/741; A61K 35/744; A61K 35/745; A61K 35/37; A61K 9/48; A61K 9/4816; A61K 38/13; A61K 8/99; A61K 2035/11; A61K 2035/115; A61K 38/18; A61K 38/19; A61K 9/0058; A61K 9/2095; A61K 9/28; A61K 9/4891; A61K 2039/521; A61K 2039/522; A61K 2039/55594; A61K 2039/585; A61K 31/047; A61K 39/02; A61K 39/39; A61K 8/345; A61K 9/0056; A61K 9/1652; Y02A 50/30; A61P 1/04; A61P 1/00; A61P 1/12; A61P 31/04; A61P 1/02; A61P 1/14; A61P 29/00; A61P 31/00; A61P 35/00; A61P 37/04; A61P 3/04; A61P 3/10; A61P 43/00; C12N 1/20; A23L 33/135; A23L 33/127; A61Q 11/00; A23P 10/30; A23V 2002/00; A23G 4/12; A23G 4/123; A61C 15/02; A61C 15/041
See application file for complete search history.

(56) References Cited

U.S. PATENT DOCUMENTS

| | | | |
|---|---|---|---|
| 9,028,841 B2* | 5/2015 | Henn | A61K 9/4891 424/247.1 |
| 2008/0268006 A1 | 10/2008 | Molin et al. | |
| 2009/0208469 A1 | 8/2009 | Alenfall et al. | |
| 2010/0028449 A1 | 2/2010 | Prakash et al. | |
| 2013/0209374 A1 | 8/2013 | Cune Castellana | |
| 2014/0023620 A1 | 1/2014 | Ioudina | |
| 2014/0065218 A1 | 3/2014 | Lang et al. | |
| 2014/0199281 A1* | 7/2014 | Henn | A61K 9/4891 424/93.46 |
| 2015/0238548 A1 | 8/2015 | Huang et al. | |
| 2015/0240200 A1 | 8/2015 | Tsai et al. | |
| 2015/0250834 A1 | 9/2015 | Tsai et al. | |

(Continued)

FOREIGN PATENT DOCUMENTS

| | | |
|---|---|---|
| CN | 101190239 A | 6/2008 |
| CN | 101703179 A | 5/2010 |
| CN | 101715908 A | 6/2010 |

(Continued)

OTHER PUBLICATIONS

International Search Report and Written Opinion dated Oct. 17, 2019 for corresponding PCT Application No. PCT/EP2019/067007.
Office Action dated Oct. 18, 2019 in co-pending U.S. Appl. No. 16/070,573.
Office Action dated Apr. 2, 2020 in co-pending U.S. Appl. No. 16/070,553.
Non-Final Office Action dated Sep. 18, 2020 in the co-pending U.S. Appl. No. 16/070,553.
Johannes Snel et al., "Competitive Selection of Lactic Acid Bacteria That Persists in the Human Oral Cavity", Applied and Environmental Microbiology, vol. 77, No. 23, 2011, pp. 8445-8450.

(Continued)

*Primary Examiner* — Deborah K Ware
(74) *Attorney, Agent, or Firm* — Polsinelli PC (57) ABSTRACT

The present invention relates to certain microorganisms or mixtures thereof for use in the treatment and/or prevention of inflammation in the oral cavity, preferably for the treatment and/or prevention of gingivitis and/or peridontitis.
In particular, the present invention relates to microorganisms or mixtures thereof for use as probiotic agents for forming co-aggregates with microorganisms associated with gingivitis and/or peridontitis.
Furthermore, the present invention provides oral pharmaceutical compositions, oral care products or products for nutrition or pleasure comprising one or more of the probiotic microorganisms as active agents as well as a method of production thereof.

7 Claims, 4 Drawing Sheets

(56) References Cited

U.S. PATENT DOCUMENTS

| | | | |
|---|---|---|---|
| 2015/0328141 A1 | 11/2015 | Reindl et al. | |
| 2017/0306289 A1 | 10/2017 | Chung et al. | |

FOREIGN PATENT DOCUMENTS

| | | |
|---|---|---|
| CN | 102470151 A | 5/2012 |
| CN | 104814983 A | 8/2015 |
| DE | 202009011379 U1 | 12/2010 |
| EP | 1634948 A1 | 3/2006 |
| EP | 1955702 A1 | 8/2008 |
| EP | 2364712 A1 | 9/2011 |
| EP | 2420580 A1 | 2/2012 |
| JP | 2008502714 A | 1/2008 |
| JP | 2014516957 A | 11/2012 |
| JP | 2014000039 A | 1/2014 |
| JP | 6538286 B2 | 7/2019 |
| KR | 1020120035923 A | 4/2012 |
| WO | 0078322 A2 | 12/2000 |
| WO | 2010077795 A2 | 7/2010 |
| WO | 2010099824 A1 | 9/2010 |
| WO | 2012022773 A1 | 2/2012 |
| WO | 2012033151 A1 | 3/2012 |
| WO | 2010064373 A1 | 5/2012 |
| WO | 2012156491 A1 | 11/2012 |
| WO | 2014140080 A1 | 9/2014 |
| WO | 2017035412 A1 | 3/2017 |
| WO | 2017125447 A1 | 7/2017 |
| WO | 2017125453 A1 | 7/2017 |

OTHER PUBLICATIONS

International Search Report and Written Opinion dated Mar. 17, 2017 in corresponding PCT Application No. PCT/EP2017/051005.
Biogrowing: "Dietary Supplements", 2010, pp. 1-3, XP002758028.
Li, Allen, "Biogrowing probiotics brochure", 2015, p. 1, XP002758029.
Iqbal, S. et al., "ß-Galactosidase from Lactobacillus plantarum WCFS1: biochemical characterization and formation of prebiotic galacto-oligosaccharides," Carbohydrate Research, vol. 345, 2010, pp. 1408-1416.
International Preliminary Report on Patentability dated Jul. 24, 2018 for corresponding PCT Application No. PCT/EP2017/051011.
International Search Report and Written Opinion dated Mar. 10, 2017 for corresponding PCT Application No. PCT/EP2017/051011.
Anonymous: "Biogrowing—comprehensive probiotic solutions provider," 2015, XP002759385, pp. 1-16 www.biogrowing.com.
Sookkhee, S. et al., "Lactic acid bacteria from healthy oral cavity of Thai volunteers: Inhibition of oral pathogens," Journal of Applied Microbiology, vol. 90, No. 2, 2001, pp. 172-179.
Vuotto, Claudia et al., "Probiotics to counteract biofilm-associated infections: promising and conflicting data," International Journal of Oral Science, vol. 6, No. 4, 2014, pp. 189-194.
Chuang, Li-Chuan et al., "Probiotic effect on cariogenic bacterial flora," Clinical Oral Investigations, vol. 15, No. 4, 2010, pp. 471-476.
Korean Office Action dated Oct. 18, 2018 for corresponding Korean Patent Application No. 10-2018-7023803.
Chinese Office Action dated Jan. 11, 2019 for corresponding Chinese Patent Application No. 201780007278.3.
Chinese Office Action dated Apr. 3, 2019 for corresponding Chinese Application No. 201780007278.3.
Kistler, James O. et al.; "Development and pyrosequencing analysis of an in-vitro oral biofilm model," BMC Microbiology; 2015, pp. 1-10.
Japanese Office Action dated Dec. 10, 2018 for corresponding JP Application No. JP 2018-538205.
Australian Office Action dated Sep. 10, 2018 for corresponding AU Application No. 2017208481.
European Office Action dated Mar. 8, 2018 for corresponding EP Application No. EP 16151963.2.
Written Opinion dated Mar. 22, 2019 for corresponding PCT Application No. PCT/EP2018/067090.
Written Opinion dated Jul. 27, 2017 for corresponding PCT Application No. PCT/EP2017/051003.
International Search Report and Written Opinion dated Mar. 16, 2018, for corresponding PCT Application No. PCT/EP2018/051112.
Snel, J. et al., "Competitive Selection of Lactic Acid Bacteria That Persists in the Human Oral Cavity", Applied and Environmental Microbiology, vol. 77, No. 23, 2011, pp. 8445-8450 XP055379435.
Roy, Byun et al., "Quantitative analysis of diverse Lactobacillus species present in advanced dental caries", Journal of Clinical Microbiology, American Society of Microbiology, vol. 42, No. 7, 2004, pp. 3128-3136 XP002488329.
Azcarate-Peril, M. A. et al., "Analysis of the Genome Sequence of Lactobacillus gasseri ATCC 33323 Reveals the Molecular Basis of an Autochthonous Intestinal Organism", Applied and Environmental Microbiology, vol. 74, No. 15, 2008, pp. 4610-4625 XP055029769.
European Office Action dated Mar. 12, 2021 for corresponding European Application No. 18702144.9.
Mette Kirstine Keller et al., "Co-aggregation and growth inhibition of probiotic lactobacilli and clinical isolates of mutans streptococci: An in vitro study," Acta Odontologica Scandinavica, vol. 69, 2011, pp. 263-268 XP009162555.
Zhihong Sun et al., "Expanding the biotechnology potential of lactobacilli through comparative genomics of 213 strains and associated genera," Nature Communications, 2015, pp. 1-13 XP002769022.
S. Resta-Lenert et al., "Live probiotics protect intestinal epithelial cells from the effects of infection with enteroinvasive Escherichia coli (EIEC)," Inflammatory Bowel Disease, vol. 52, 2003, pp. 988-997 XP055678154.
Tamara Smokvina et al., "Lactobacillus paracasei Comparative Genomics: Towards Species Pan-Genome Definition and Exploitation of Diversity," PLoS One, vol. 8, Issue 7, 2013, pp. 1-18 XP055711380.
C. Lang et al., "Specific Lactobacillus/Mutans Streptococcus Co-aggregation," Research Reports, vol. 89, No. 2, 2009, pp. 175-180 XP009162445.
U.S. Appl. No. 16/070,553, filed Jul. 17, 2018.
U.S. Appl. No. 16/070,573, filed Jul. 17, 2018.
PCT/EP2018/067090, Jun. 26, 2018.
PCT/EP2017/051003, Jan. 18, 2017.
PCT/EP2019/067007, Jun. 26, 2019.
U.S. Appl. No. 17/254,347, filed Dec. 21, 2020.
Japanese Office Action dated Jan. 14, 2021 for corresponding Japanese Application No. 2018-538221.

* cited by examiner

PROBIOTICS FOR AGGREGATION WITH DISEASE-ASSOCIATED SPECIES IN THE ORAL CAVITY

CROSS-REFERENCE TO RELATED APPLICATIONS

This application is a national stage application (under 35 U.S.C. § 371) of PCT/EP2018/051112, filed Jan. 17, 2018, which claims benefit of European Application No. 17152068.7, filed Jan. 18, 2017, which are incorporated herein by reference in their entireties.

The present invention relates to certain microorganisms or mixtures thereof for use in the treatment and/or prevention of inflammation in the oral cavity, preferably for the treatment and/or prevention of gingivitis and/or peridontitis.

In particular, the present invention relates to microorganisms or mixtures thereof for use as probiotic agents for forming co-aggregates with microorganisms associated with gingivitis and/or peridontitis, in particular with oral bacterial species selected from the group consisting of *Porphyromonas gingivalis*, *Porphyromonas endodontalis*, *Tannerella forsythia*, *Filifactor alocis* and *Eubacterium saphenum*.

Furthermore, the present invention provides oral pharmaceutical compositions, oral care products or products for nutrition or pleasure comprising one or more of the probiotic microorganisms as active agents as well as a method of production thereof.

Inflammatory conditions of the gums are primarily induced by the formation of dental plaque. Colonizing bacteria form a biofilm on the surface of the teeth aided by the presence of food residues as well as components of saliva. If not sufficiently cleared away at an early stage, plaque films on the surface of the teeth result in deposition of dental calculus which is very hard to remove. The presence of raised numbers of bacteria at the gingival margin leads to inflammation of the gingivae, known as gingivitis. In susceptible individuals, gingivitis may progress to peridontitis, which can lead to tooth loss. In particular, lipopolysaccharides (LPS) present in Gram-negative bacteria can cause a non-specific immune response by LPS-stimulated macrophages, which release prostaglandin E2 (PEG2) and pro-inflammatory mediators such as interleukins and TNF-α in the affected tissue. The pro-inflammatory mediators induce the release of further PGE2s and matrix metalloproteinases (MMPs) from the residing fibroblasts, which destroy the extracellular matrix of the surrounding tissue. This allows bacteria to penetrate deeper into the tissue and promote the inflammatory process independent of the outer layer of the epithelium and the dental root causing the formation of a periodontal pocket. The alveolar bone supporting the tooth resorbs ahead of the advancing bacteria, causing the tooth to become unstable and, if left untreated, lost.

In order to avoid progressive destruction of the gums, inflammatory responses in the oral cavity need to be suppressed in the early stages or ideally prevented.

Many different approaches have addressed this problem, ranging from improved methods for the mechanical removal of plaque to the use of oral care products with strong anti-bacterial properties.

However, not all the bacteria present in the oral cavity are disease-associated and many even promote oral health. Therefore, it is desirable to establish a balance towards a healthy composition of the mouth microbiota instead of nonspecifically eradicating resident bacteria.

The normal oral microbiota is highly complex and includes over 700 bacterial species as well as archaea, fungi, protozoa and viruses.

Lower gut commensals such as lactobacilli and bifidobacteria have been shown to have beneficial effects on gut health, including some anti-inflammatory properties, when administered as probiotics.

Probiotic action of bacteria in the oral cavity has been subject to some research but it has been found to vary strongly with the species used and suitable parameters for efficient application are hard to establish because the action may rely on largely unrelated effects.

Among the probiotic actions, general anti-bacterial effects against disease-associated species, the reduction or prevention of bacterial adhesion to the surface of the teeth as well as anti-inflammatory effects have been discussed in the literature.

WO 2010/077795 A2 relates to compositions to improve oral health comprising a therapeutically effective amount of beneficial bacteria selected from specific strains of streptococci and lactobacilli. The prevention of gingivitis and plaque by balancing the mouth flora towards beneficial bacteria is addressed in this context.

Probiotics containing teeth and oral care products are disclosed as being capable of preventing parodontits and gingivitis according to DE 20 2009 011 370 U1, which recites a large variety of probiotic bacteria including lactobacilli, bifidobacteria, enterococci, sporolactobacilli and streptococci. Specific strains are not mentioned, however, and the mechanism of the alleged probiotic action is not further evaluated.

WO 2010/008879 A2 provides a confectionary composition containing an inactive probiotic, which is activable upon contact with water. As probiotics, different strains of lactobacilli and bifidobacteria are disclosed. Probiotic effects mentioned in WO 2010/008879 A2 include the reduction of gum inflammation for example by suppressing pathogenic bacteria.

EP 1 852 122 A1 relates to dental and gingival health compositions containing dehydrated, reactivable microorganisms. It is explained that the microorganisms may combat virulent pathogenic bacterial flora by re-establishing the equilibirium of the affected tissue due to competition. WO 2005018342 also refers to a competition effect whereby probiotic bacteria are able to inhibit colonization or out growth of a pathogen by competing for nutrients or attachment sites.

However, it has been established, that, besides a mere competitive displacement, probiotic bacteria may be capable to form co-aggregates with the pathogens which are easily flushed out of the mouth and thus reduce the pathogen load.

The use of exogenous lactic bacteria for prophylaxis or treatment of dental caries, dental plaque and periodontal infection is disclosed in WO 00/09080. Colonization via specific binding to resident microflora (co-aggregation) is mentioned but the use of probiotics according to WO 00/09080 relies on the effect that certain lactic bacteria, which are not part of resident microflora, are capable of adhering directly to the pellicle of the teeth and thus displace pathogens or prevent their attachment.

The ability of probiotic bacteria to replace pathogens or form aggregates interfering with pathogen biofilm formation is mentioned in WO 2012/022773 A1. WO 2012/022773 A1, however, is primarily concerned with probiotic compositions for oral health comprising effective amounts of *Lactobacillus plantarum* CECT 7481 and *Lactobacillus brevis* CECT 7480, which are demonstrated to have antibacterial properties against certain pathogens, while a formation of co-aggregates is not evaluated.

WO 2012028759 (EP 2 612 904 A2) provides antimicrobial bacterial strains of the genus *Streptococcus* for use in treatment of infectious disease in the oral cavity, which is based on the formation of co-aggregates of *S. mutans* with the probiotic strains.

WO 2012/100991 discloses the use of binder organisms (lactic acid bacteria) to bind streptococci in the oral cavity, which are then flushed out thus preventing colonization by the pathogens and the formation of caries. Effective binder organisms according to WO 2012/100991, are certain strains of *Lactobacillus paracasei* and *Lactobacillus rhamnosus*.

While the effect of probiotic bacteria to form aggregates with streptococci has been reported in the prior art, known probiotic bacterial strains have never been evaluated individually with respect to their ability to aggregate with other oral bacteria. In particular, peridontitis-associated bacteria such as *Porphyromonas gingivalis, Porphyromonas endodontalis, Tannerella forsythia, Filifactor alocis* and *Eubacterium saphenum* are to be considered highly relevant in this context. In the extensive investigations leading up to the present invention, certain strains have been found to strongly aggregate with the above mentioned pathogens and have therefore been identified as highly efficient active agents for use in the treatment and/or prevention of gingivitis and/or peridontitis. Remarkably, many closely related strains of acknowledged probiotic bacteria show no or barely any aggregation with the disease-associated species. Thus, the present invention now allows to optimize the use of (commercially) available probiotic bacteria by selecting and/or combining the over-all most efficient strains.

An objective of the present invention was to provide microorganisms or mixtures thereof which can be used in highly effective treatment and/or prevention of inflammation in the oral cavity, in particular in the treatment and/or prevention of gingivitis and/or peridontitis.

A further objective of the present invention was to provide microorganisms or mixtures thereof which can be used as probiotic agent for forming co-aggregates with oral bacterial species associated with gingivitis and/or peridontitis, in particular with species selected from the group consisting of *Porphyromonas gingivalis, Porphyromonas endodontalis, Tannerella forsythia, Filifactor alocis* and *Eubacterium saphenum*.

Oral care compositions or products for delivering the microorganism according to the invention and a method for producing such compositions or products are also provided.

The objective of the present invention is met by a microorganism or mixture comprising or consisting of two or more microorganisms for use in the treatment and/or prevention of gingivitis and/or peridontitis, wherein the microorganism(s) is/are selected from the group consisting of *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431).

By extensive screenings, the bacterial strains according to the invention have been found to form aggregates as recited above while surprisingly many closely related strains fail to show any aggregation with the pathogens. The prior art has not evaluated the efficacy of different bacterial strains with respect to the formation of aggregates with the mentioned pathogens. In the context of the present invention, an aggregation index has been individually determined for the tested probiotic strains to allow direct selection of the most potent strains for application in oral care.

The strain *Lactobacillus delbrueckii* subsp. *lactis* LL-G41 has been deposited under the Budapest Treaty at the China Center for Type Culture Collection (CCTCC), Wuhan University, Wuhan 430072, China under the accession number CCTCC M 2016652 by BioGrowing Co., Ltd., No. 10666 Songze Rd., Qingpu Shanghai 201700, China, on 17 Nov. 2016. The strain *Lactobacillus* fermentum 35D has been deposited under the Budapest Treaty at the Leibniz Institut Deutsche Sammlung von Mikroorganismen and Zellkulturen GmbH (DSMZ), lnhoffenstr. 7B, 38124 Braunschweig, Germany, under the accession number DSM 32130 by Probi AB, Solvegatan 41, 22370 Lund, Sweden, on 2 Sep. 2015. The strains *Lactobacillus gasseri* NS8 (NCIMB 11718; date of accession 27 Jan. 1982, deposited by DSMZ) and *Lactobacillus salivarius* NS13 (NCIMB 8816; date of accession 1 Oct. 1956, deposited by University of Birmingham) are publicly available at the National Collection of Industrial, Food and Marine Bacteria (NCIMB), Ferguson Building, Craibstone Estate, Bucksburn, Aberdeen AB21 9YA, United Kingdom, under the accession number NCIMB 11718 and NCIMB 8816, respectively. The strains *Streptococcus salivarius* NS18 and *Streptococcus salivarius* NS19 have been deposited under the Budapest Treaty in the CBS collection at the Westerdijk Fungal Biodiversity Institute, Uppsalalaan 8, 3584 AD Utrecht, The Netherlands, under the accession numbers CBS 142430 and CBS 142431 by NIZO Food Research BV, Kernhemseweg 2, 6718 ZB Ede, The Netherlands, on 8 Mar. 2017.

A number of different strains have been tested for their binding capacity to pathogens and were classified into categories according to their aggregation index as explained in the example section below.

Microorganism(s) according to the invention may preferably be used as probiotic agent for forming co-aggregates with oral bacterial species associated with gingivitis and/or peridontitis, in particular with disease-associated species selected from the group consisting of *Porphyromonas gingivalis, Porphyromonas endodontalis, Tannerella forsythia, Filifactor alocis* and *Eubacterium saphenum*.

The recited disease-associated species are known to be involved in the development of peridontitis and associated diseases and therefore are highly desirable target disease-associated species for aggregation.

The colonization of the oral mucosa by pathogenic bacteria and the formation of plaque can tip the microbial balance in the oral cavity towards an accumulation of detrimental microorganisms, which is also referred to as dysbiosis. Therefore, the microorganisms for use in the prevention and/or treatment of inflammation in the oral cavity according to the invention includes the use in the prevention and/or treatment of plaque and plaques associated diseases and conveniently aides to balance the mouth flora towards a healthy state by promoting removal of the disease associated species from the mouth.

In a preferred embodiment of the present invention, the microorganism(s) described above is/are (an) attenuated or (a) dead microorganism(s), preferably (a) heat-inactivated microorganism(s), preferably (a) microorganism(s) heat-inactivated by incubation for 2 to 8 minutes at a temperature between 70 and 100° C.

Advantageously, it is also possible to use dead or, for example, heat-inactivated microorganisms as merely certain membrane structures of the cells are required to promote aggregation.

In a further aspect of the present invention, the microorganism according to the invention additionally has/have an inhibitory activity on the growth of disease-associated species, in particular on the growth of one or more disease-associated species selected from the group consisting of *Porphyromonas gingivalis, Porphyromonas endodontalis, Tannerella forsythia, Filifactor alocis, Eubacterium saphenum, Parvimonas micra, Lachnoanaerobaculum saburreum*, when the microorganism is *Lactobacillus salivarius* NS13 (NCIMB 8816).

Advantageously, probiotic strains according to the invention, may, in addition to the anti-inflammatory activity, also exhibited growth-inhibiting effects on certain disease-associated species as demonstrated in the examples below.

In one aspect, the present invention relates to the microorganism(s) recited above, wherein the microorganism(s) are additionally capable of treating and/or preventing inflammation in the oral cavity, preferably for reducing or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB, wherein the microorganism(s) is/are selected from the group consisting of *Lactobacillus delbrueckii* subsp. *lactis* LL-G41 (CCTCC M 2016652), *Lactobacillus fermentum* 35D (DSM 32130) and *Lactobacillus salivarius* NS13 (NCIMB 8816).

To cover further probiotic effects of the microorganisms according to the invention, unrelated to the formation of aggregates with disease-associated species, is has been elucidated individually which probiotic strains are capable of efficiently inhibiting the release of a number of different pro-inflammatory factors. It is therefore possible to optimize the use of commercially available probiotic strains for the treatment and/or prevention of inflammatory conditions in the oral cavity be selecting the overall most efficient strain(s) with respect to multiple probiotic actions.

According to another aspect of the present invention, fragments of one or more microorganism(s) as defined in any of the aspects described above may be used in the treatment and/or prevention of inflammation in the oral cavity, preferably in the treatment and/or prevention of gingivitis and/or peridontitis, preferably for use as probiotic agent for forming co-aggregates with oral bacterial species associated with gingivitis and/or peridontitis, in particular with disease-associated species selected from the group consisting of *Porphyromonas gingivalis, Porphyromonas endodontalis, Tannerella forsythia, Filifactor alocis* and *Eubacterium saphenum*.

It is not necessary to use whole cells of the probiotic microorganisms according to the invention as mixtures comprising only fragments (e.g. debris of degraded cells), in particular membrane fractions of the microorganisms, are sufficient to provide the inventive effects. In the context of the present invention, "fragments of one or more microorganism(s)" therefore preferably refers to any part(s) or combination of parts of a cell that is/are capable of providing the aggregation effect described herein.

In a further aspect, the present invention also relates to an oral pharmaceutical composition, oral care product or product for nutrition or pleasure, comprising one or more microorganism(s) selected from the group consisting of *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431) or fragments thereof, wherein the total amount of the microorganism(s) or the fragments thereof is sufficient for treating and/or preventing gingivitis and/or peridontitis, preferably by forming co-aggregates with oral bacterial species associated with gingivitis and/or peridontitis, in particular with disease-associated species selected from the group consisting of *Porphyromonas gingivalis, Porphyromonas endodontalis, Tannerella forsythia, Filifactor alocis* and *Eubacterium saphenum*, further preferably wherein the total amount of the microorganism(s) or the fragments thereof is in the range from 0.01 to 100%, more preferably in the range from 0.1 to 50%, most preferably in the range from 1 to 10%, in each case with respect to the total weight of the composition, and/or wherein the total amount of the microorganism(s) or the fragments thereof is in the range from $1 \times 10^3$ to $1 \times 10^{11}$ colony forming units (CFU), more preferably in the range from $1 \times 10^5$ to $1 \times 10^{10}$ CFU.

The skilled person is aware that the probiotic organisms used in a composition or product according to the present invention represent biologic material the activity of which may vary with the batch and depend also on the production or processing method. Therefore, the suitable amount can be adjusted accordingly within the given range.

Products for pleasure are products that are consumed for the purpose of enjoyment such as e.g. confectionery (e.g. chocolates, chocolate bar products, other bar products, fruit gums, hard-boiled sweets, toffees, chewing gum, ice cream), alcoholic or non-alcoholic beverages (e.g. coffee, tea, wine, wine-containing beverages, beer, beer-containing beverages, liqueurs, spirits, brandies, fruit-containing lemonades, isotonic beverages, refreshing beverages, nectars, fruit and vegetable juices, fruit or vegetable juice preparations).

Furthermore, the present invention relates to a composition or product as described above for use in the treatment and/or prevention of inflammation in the oral cavity, preferably for use in the treatment and/or prevention of gingivitis and/or peridontitis, preferably for use as probiotic agent for forming co-aggregates with oral bacterial species associated with gingivitis and/or peridontitis, in particular with disease-associates species selected from the group consisting of *Porphyromonas gingivalis, Porphyromonas endodontalis, Tannerella forsythia, Filifactor alocis* and *Eubacterium saphenum*.

A composition according to the invention may further comprise one or more components selected from the group consisting of carriers, excipients or further active ingredients such as, for example, active agents from the group of nonsteroidal antiphlogistics, antibiotics, steroids, anti-TNF-alpha antibodies or other biotechnologically produced active agents and/or substances as well as analgetics, dexpanthenol, prednisolon, polyvidon iodide, chlorhexidine-bis-D-gluconate, hexetidine, benzydamine HCl, lidocaine, benzocaine, macrogol lauryl ether, benzocaine in combination with cetidyl pyridinium chloride or macrogol lauryl ether in combination with protein free hemodialysate from calf blood, as well as for example fillers (e.g. cellulose, calcium carbonate), plasticizer or flow improves (e.g. talcum, magnesium stearate), coatings (e.g. polyvinyl acetate phtalate, hydroxyl propyl methyl cellulose phtalate), disintegrants (e.g. starch, crosslinking polyvinyl pyrrolidone), softener (e.g. triethyl citrate, dibutyl phthalate) substances for granulation (lactose, gelatin), retardation (e.g. poly (meth)acrylic acid methyl/ethyl/2-trimethyl aminomethyl ester copolymerizates in dispersion, vinyl acetate/crotonic acid copolymerizates), compaction (e.g. microcrystalline cellulose, lactose), solvents, suspending or dispersing agents (e.g. water, ethanol), emulsifiers (e.g. cetyl alcohol, lecithin), substances for modifying the rheological properties (silica, sodium alginate), substances for microbial stabilization (e.g. benzalkonium chloride, potassium sorbate), preservatives and antioxidants (e.g. DL-alpha-tocopherol, ascorbic acid) substances for modifying pH (lactic acid, citric acid), blowing agents or inert gases (e.g. fluorinated chlorinated hydrocarbons, carbon dioxide), dyes (iron oxide, titanium oxide), basic ingredients for ointment (e.g. paraffines, bees wax) and others as described in the literature (e.g. in Schmidt, Christin. Wirk- und Hilfsstoffe für Rezeptur, Defektur und Graherstellung. 1999; Wissenschaftliche Verlagsgesellschaft mbH Stuttgart oder Bauer, Frömming Führer. Lehrbuch der Pharmazeutischen Technologie. 8. Auflage, 2006. Wissenschaftliche Verlagsgesellschaft mbH Stuttgart).

A composition or product according to the present invention may also be coated or encapsulated.

Encapsulation of a composition according to the invention may have the advantage of allowing a controlled release, for example upon contact with water, or a continuous release over an extended period of time. Moreover, the composition may be protected from degradation improving the shelf life of the product. Methods for encapsulation of active ingredients are well known in the art and a number of encapsulation materials as well as methods how to apply them to a composition according to specific requirements are available.

Furthermore, a composition or product according to the invention may be in the form of a solution, suspension, emulsion, tablets, granules, powder or capsules.

The composition or product according to the invention may be selected form the group consisting of toothpaste, tooth gel, tooth powder, tooth cleaning liquid, tooth cleaning foam, mouth wash, mouth spray, dental floss, chewing gum and lozenges.

Such compositions or products may contain abrasive systems (abrasive and/or polishing components) such as silicates, calcium carbonate, calcium phosphate, aluminum oxide and/or hydroxyl apatite, surfactants such as e.g. sodium lauryl sulfate, sodium lauryl sarcosinate and/or cocamidopropyl betaine, humectants such as glycerol and/or sorbitol, thickening agents, e.g. carboxy methyl cellulose, poly ethylene glycols, carrageenans and/or Laponite®, sweeteners such as saccharine, aroma and taste correcting agents for unpleasant taste impressions, taste modifying substances (e.g. inositol phosphate, nucleotides, e.g. guanosine monophosphate, adenosine monophosphate or other substances, e.g. sodium glutamate or 2-phenoxy propionic acid), cooling agents such as menthol derivates (e.g. L-mentyl lactate, L-menthyl alkyl carbonate, menthone ketals), icilin and icilin derivates, stabilizers and active agents such as sodium fluoride, sodium monofluoro phosphate, tin difluoride, quarternary ammonium fluorides, zinc citrate, zinc sulfate, tin pyrophosphate, tin dichloride, mixtures of different pyrophosphates, triclosane, cetyl pyridinium chloride, aluminum lactate, potassium citrate, potassium nitrate, potassium chloride, strontium chloride, hydrogen peroxide, aroma substances, sodium bicarbonate and/or smell correcting agents.

Chewing gums or dental care chewing gums may comprise a chewing gum base comprising elastomers, e.g. polyvinyl acetate (PVA), polyethylene, (low or medium molecular) polyiso butane (PIB), polybutadiene, isobutene/isoprene copolymers, polyvinyl ethyl ether (PVE), polyvinyl butyl ether, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate and mixtures of the mentioned elastomers as e.g. example described EP 0 242 325, U.S. Pat. Nos. 4,518,615, 5,093,136, 5,266,336 5,601,858 or U.S. Pat. No. 6,986,709. Additionally chewing gum bases may contain further ingredients, e.g. (mineral) filers, e.g. calcium carbonate, titanium dioxide, silicone dioxide, talcum, aluminum oxide, dicalcium phosphate, tricalcium phosphate, magnesium hydroxide and mixtures thereof, plasticisers (e.g. lanolin, stearic acid, sodium stearate, ethyl acetate, diacetin (glycerol diacetate), triacetin (glycerol triacetate) and triethyl citrate), emulsifiers (e.g. phosphatides, such as lecithin and mono and diglycerides of fatty acids, e.g. glycerol monostearate), antioxidants, waxes (e.g. paraffine waxes, candelilla waxes, carnauba waxes, microcrystalline waxes and polyethylene waxes), fats or fatty oils (e.g. hardened (hydrogenated) plant or animal fats) and mono, di or triglycerides.

Finally, the present invention also relates to a method of producing an oral pharmaceutical composition, an oral care product or a product for nutrition or pleasure as described above, comprising the following step:

combining one or more microorganism(s), selected from the group consisting of *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431) or fragments thereof to one or more further components, preferably to one or more components selected form the group consisting of carriers, excipients or further active ingredients.

In the context of the present invention, also described herein is a method of treating a subject or, respectively, patient, in particular for treating and/or preventing of inflammation in the oral cavity (as described herein), comprising administering the herein described microorganisms or mixtures to a subject/patient, preferably to a subject/patient in need thereof, preferably in an amount sufficient to treat or prevent inflammation, preferably to treat or prevent gingivitis and/or peridontitis.

The following examples are added to illustrate the present invention without being intended to limit the scope.

SHORT DESCRIPTION OF THE FIGURES

$OD_{total}$=$OD_{target\ strain}$+$OD_{probiotic\ strain}$. Aggregation indices are represented by grouped columns for each of the probiotics *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431) from left to right and within each group the columns for the *Porphyromonas gingivalis* strains represent ATCC 33277T, 1807 (wt), 2836 (wt), 7681 (wt), 2103 (wt) and 9066 (wt) from left to right.

EXAMPLE 1: ESTABLISHING THE CULTIVATION AND HANDLING OF PROBIOTIC STRAINS

In order to identify the optimal growth conditions and points of harvest and to determine the colony forming units (CFU) for the probiotic bacteria to be screened, first the log phase and the end of the growth phase were determined.

Bacterial Growth

The frozen (−80° C.) pro-biotic stocks were thawed over night at 4° C. and 6 ml of sterile 9% NaCl solution added to the 1.2 ml of bacteria at the next morning. The samples were centrifuged (5 min, 5000 rpm), the supernatant discarded, the pellet washed with 8 ml 9% NaCl and again centrifuged for 5 min at 5000 rpm. The pellet was then resuspended in 1.2 ml 9% NaCl and 1 ml of the sample added to 50 ml 37° C. warm media (MRS Bouillon, Carl Roth KG, Karlsruhe) and incubated at 37° C. The incubations were performed in a 50 ml sterile polypropylen tube (Greiner) and probes were harvested at different time points to evaluate the growth curve.

OD-Determination

For determination of OD, 500 µl of the bacterial suspension were removed and diluted in 1 ml MRS Bouillon in a 1.5 ml-PS-cuvette (Brand). OD-determination was performed at 600 nm (ThermoScientific, Helios Epsilon) 1.5 ml MRS Bouillon were used as blanc.

Determination of CFU

For determination of CFU, bacteria were diluted (1:10.000.000, 1:50.000.000 and 1:100.000.000), plated on MRS-agar-plates (MRS Agar, X924, Carl Roth) and incubated for 2 days at 37° C. The grown colonies were then counted and the CFU was calculated.

The bacteria approached the log phase right from the beginning until 7 to 8 hours when they start to reach the plateau phase. The amount of bacteria to be seeded does not change the shape of the curve. 5 hours were chosen as the point at the steepest growing phase to harvest the bacteria in the log phase and 7 hours to harvest them at the end of the log phase.

EXAMPLE 2: CO-AGGREGATION OF PROBIOTIC STRAINS WITH ORAL DISEASE-ASSOCIATED BACTERIA

The screening was based on the proprietary OASSYS® co-aggregation. The target strain and probiotic strains were cultivated in specific growth conditions, harvested, washed and co-incubated. The behavior of the strains was monitored:

a) macroscopically, for an appearance of flocculation that was graded 0-3 (with "0" for no flocculation/cloudy supernatant and "3" for a considerable pellet/clear supernatant)

b) by estimation of the aggregation index (% aggregation), which expresses the percentage of applied bacterial cells that have aggregated after co-incubation. If aggregation has taken place, the aggregates will sink to the well bottom when slightly centrifuged, resulting in a supernatant of decreased optical density (measured photometrically at 600 nm) than in case of no interaction between the strains, where optical density of the supernatant will remain unchanged. This approach allows accurate quantification of an aggregation event.

The aggregation index was calculated according to the formula:

$$\text{Aggregation index } (\%) = \frac{OD_{(total)} - OD_{(supernatant)}}{OD_{(total)}} \times 100$$

$$OD_{(total)} = OD_{(target\ strain)} + OD_{(priobiotic\ strain)}$$

The tested strains were then classified into 5 categories according to their aggregation index (Table 1). A low aggregation index indicates low grade of stable interaction and aggregation between cells, while a high aggregation index indicates high aggregation capacity and little or no planktonic cells left after co-incubation. In the context of the present invention, it is preferred that the microorganisms used according to the present invention show an aggregation index of at least 60%, preferably at least 80%, against a disease-associated microorganism (as described herein).

TABLE 1

| | Aggregation Index [%] | | | | |
|---|---|---|---|---|---|
| | 0-20% | 20-40% | 40-60% | 60-80% | 80-100% |
| Aggregation category | 1 | 2 | 3 | 4 | 5 | c) (optional) light microscopy; selected strains for that a visible flocculation has been observed, were analysed by light microscopy and photographed.

Cultivation and Characterization of Target Strains

Microbiological methods for cultivation and handling of the target bacteria *Eubacterium saphenum*, *Tanarella forsythia*, *Filifactor alocis*, *Porphyromonas endodontails* and *Porphyromonas gingivalis* were established and adapted.

The target strains were delivered as bacterial suspension in broth, flushed from an agar plate and collected in a cryotube. To establish the most suitable growth medium for cultivation of the target strains as suspension culture, a variety of media, such as BHI (Brain Heart Infusion), TYP (Tryptone-Yeast ExtractPeptone), FAB (Fastidious Anaerobe Broth) in some cases supplemented with arginine, cysteine, vitamine K and haemin, were prepared and tested. Optimal growth conditions were established for *P. gingivalis*, *P. endodontalis* and *F. alocis*. However, no appropriate liquid medium could be found for the cultivation of *T. forsythia* and *E. saphenum* and thus the strains were adapted to growth on solid medium (Fastidious Anaerobe Agar supplemented with horse blood and Nacetylmuramic acid). For the subsequent assay the cell material was harvested from the plates. This alternative method of cultivation resulted in lower yield in cell material and allowed conduction of only limited number of screening experiments. Therefore, the screening of *T. forsythia* was reduced to probiotic strains that have already shown positive co-aggregation capacity in screening against other disease-associated species (*F. alocis*, *P. gingivalis* and *P. endodontalis*).

Due to very slow and poor growth *E. saphenum* was completely excluded from the screening.

Screening

Co-aggregation assay was performed in 24-well plates. The target and probiotic strains were cultured, washed several times and co-incubated. Additionally, self-aggregation capacity of both analyzed probiotic and target strains was tested. For this purpose the target and probiotic strains were incubated alone and the same parameters—macroscopic observation and measurement of optical density in the supernatant—were recorded, as in case of co-incubation. To create a better overview of the co-aggregation capacity of particular strains and to facilitate hit selection, the probiotic strains were classified into categories according to their aggregation indices (see also Table 1). The presence of aggregates in several samples with a high aggregation index was confirmed by microscopical analysis.

Among the over 60 strains screened, the strains *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431) showed aggregation indices of over 60% with at least one target strain.

Figure 1:
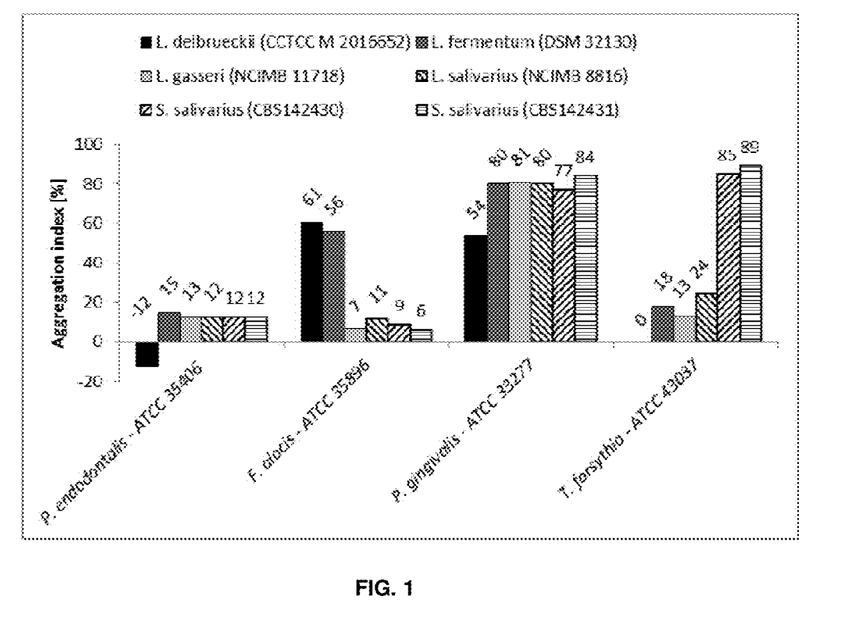
FIG. 1 shows the aggregative power of the indicated probiotics against type strains of disease-associated bacteria in a co-aggregation assay. Results feature the decrease of total optical density upon co-incubation of pathogenic and probiotic bacteria expressed as aggregation index in percent. aggregation index [%]=($OD_{total}$−$OD_{supernatant}$/$OD_{total}$)× 100; $OD_{total}$=$OD_{target\ strain}$+$OD_{probiotic\ strain}$. For each strain of disease-associated bacteria shown on the x-axis the aggregation index is represented by the columns for *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS13 (NCIMB 8816), *Streptococcus salivarius* NS18 (CBS 142430) and *Streptococcus salivarius* NS19 (CBS 142431) from left to right.
Figure 2:
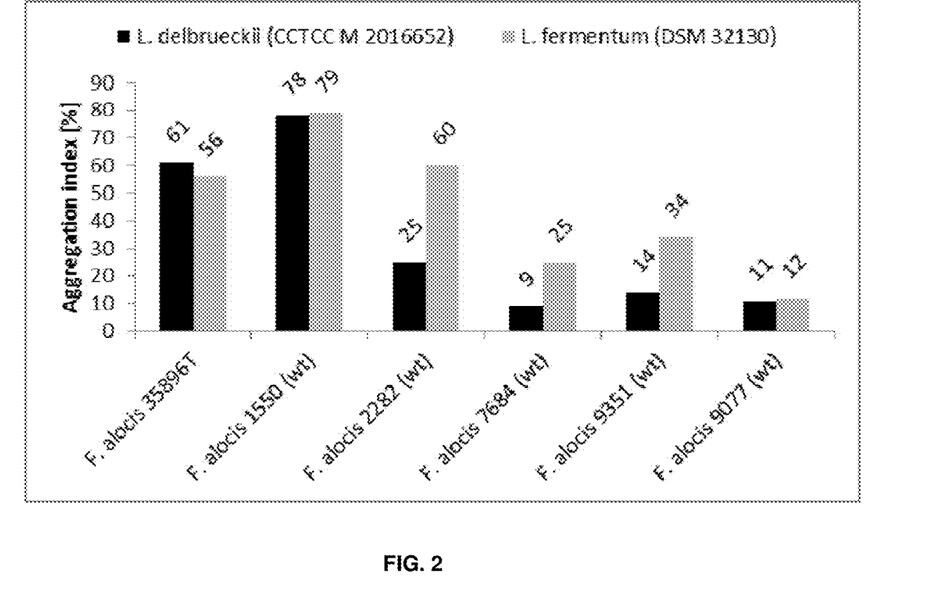
FIG. 2 shows the aggregative power of indicated probiotics against wildtype (wt) strains of disease-associated *Filifactor alocis* and type strain *Filifactor alocis* (ATCC 35896$^T$) in a co-aggregation assay. Results feature the decrease of total optical density upon co-incubation of pathogenic and probiotic bacteria expressed as aggregation index in percent. Aggregation index [%]=($OD_{total}$−$OD_{supernatant}$/$OD_{total}$))×100; $OD_{total}$=$OD_{target\ strain}$+$OD_{probiotic\ strain}$. For each wildtype (wt) strain of disease-associated *Filifactor alocis* and type strain *Filifactor alocis* (ATCC 35896$^T$) shown on the x-axis the aggregation index is represented for *Lactobacillus delbrueckii* subsp. *lactis* LL-G41 (CCTCC M 2016652) (left columns) and for *Lactobacillus fermentum* 35D (DSM 32130) (right columns).
Figure 3:
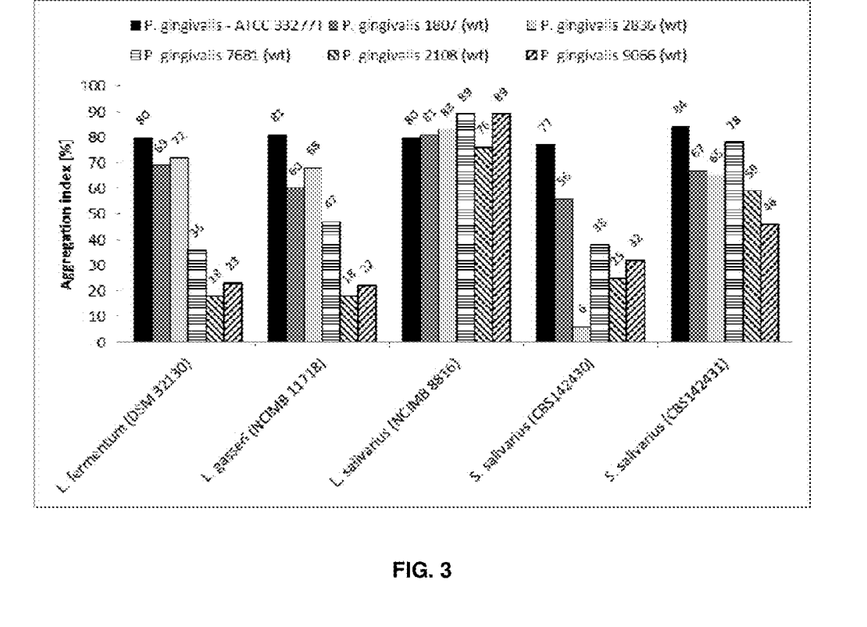
FIG. 3 shows the aggregative power of indicated probiotics against wildtype (wt) strains of disease-associated *Porphyromonas gingivalis* and type strain *Porphyromonas gingivalis* (ATCC 33277$^T$) in a co-aggregation assay. Results feature the decrease of total optical density upon co-incubation of pathogenic and probiotic bacteria expressed as aggregation index in percent. Aggregation index [%]=($OD_{total}$−$OD_{supernatant}$/$OD_{total}$)×100.
Figure 4:
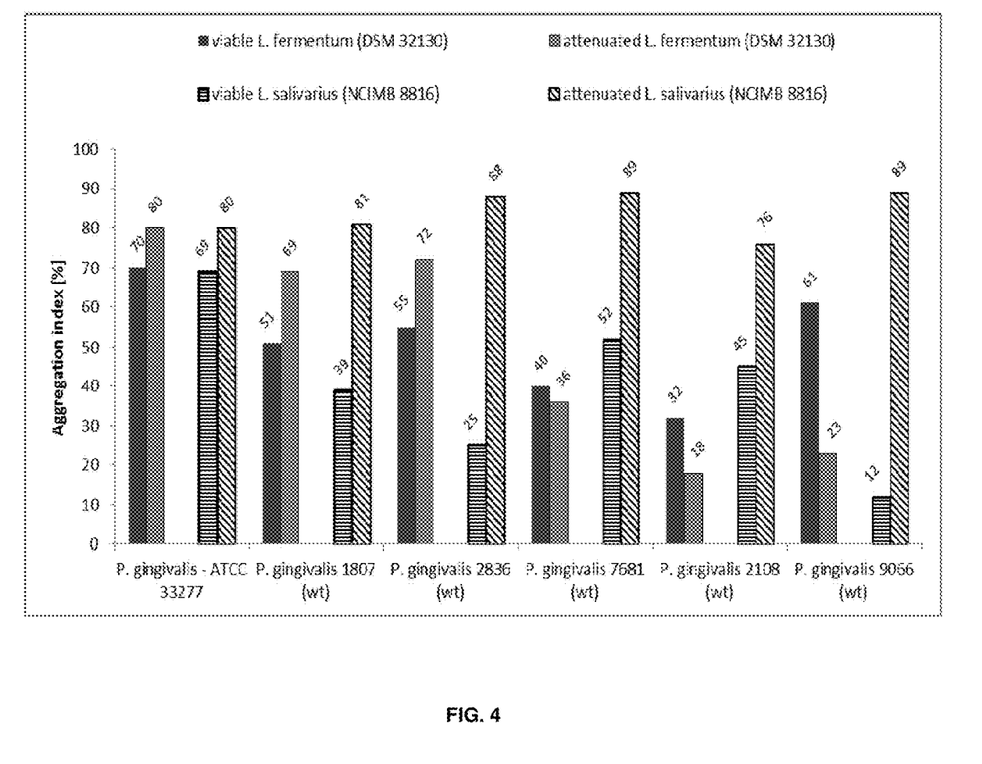
FIG. 4 shows the aggregative power of indicated viable or attenuated probiotics against wildtype (wt) strains of disease-associated *Porphyromonas gingivalis* and type strain *Porphyromonas gingivalis* (ATCC 33277$^T$) in a co-aggregation assay. Results feature the decrease of total optical density upon co-incubation of pathogenic and probiotic bacteria expressed as aggregation index in percent. Aggregation index [%]=($OD_{total}$−$OD_{supernatant}$/$OD_{total}$)×100; $OD_{total}$=$OD_{target\ strain}$+$OD_{probiotic\ strain}$. For each strain of *Porphyromonas gingivalis*, shown on the y-axis, ATCC 33277T, 1807 (wt), 2836 (wt), 7681 (wt), 2103 (wt) and 9066 (wt) from left to right, the aggregation index for viable *Lactobacillus fermentum* 35D (DSM 32130) (left columns) and attenuated *Lactobacillus fermentum* 35D (DSM 32130) (right columns) as well as viable *Lactobacillus salivarius* NS13 (NCIMB 8816) (left columns) and attenuated *Lactobacillus salivarius* NS13 (NCIMB 8816) (right columns) is shown alternately.

The aggregative power of the probiotic strains with respect to tested disease-associated strains is shown in FIGS. 1 to 4. The grading for macroscopic co-aggregation and the aggregation category for the probiotic strains is shown in tables 2 and 3.

Table 2 shows the aggregative power of indicated probiotics against wildtype (wt) strains of disease associated *Filifactor alocis* and type strain *Filifactor alocis* (ATCC 35896$^T$) in a co-aggregation assay being evaluated macroscopically. Flocculation is graded as "0" for no flocculation and "3" for a considerable pellet or clear supernatant. In addition, the table shows grading of aggregation indices within aggregation categories for easier interpretation of assay results.

TABLE 2

| Macroscopic co-aggregation | | 0-1 | | 2 | | 3 |
|---|---|---|---|---|---|---|
| | ATCC 35896$^T$ | 1550 (wt) | 2282 (wt) | 7684 (wt) | 9351 (wt) | 9077 (wt) |
| L. fermentum (DSM 32130) | 3 | 2 | 3 | 2 | 2 | 0 |
| L. delbrueckii (CCTCC M 2016652) | 3 | 3 | 3 | 1 | 3 | 0 |
| Aggregation category | 1 | 2 | 3 | 4 | | 5 |
| Aggregation index | <20% | 20-40% | 41-60% | 61-80% | | >80% |
| | ATCC 35896$^T$ | 1550 (wt) | 2282 (wt) | 7684 (wt) | 9351 (wt) | 9077 (wt) |
| L. fermentum (DSM 32130) | 4 | 4 | 3 | 2 | 2 | 1 |
| L. delbrueckii (CCTCC M 2016652) | 3 | 4 | 2 | 1 | 1 | 1 |

Table 3 shows the aggregative power of indicated probiotics against wildtype (wt) strains of disease-associated *Porphyromonas gingivalis* and type strain *Porphyromonas gingivalis* (ATCC 33277$^T$) in a co-aggregation assay being evaluated macroscopically. Flocculation is graded as "0" for no flocculation and "3" for a considerable pellet or clear supernatant. In addition, the table shows grading of aggregation indices within aggregation categories for easier interpretation of assay results.

TABLE 3

| Macroscopic co-aggregation | 0-1 | 2 | 3 | 1 | |
|---|---|---|---|---|---|
| | ATCC 33277$^T$ | 1807 (wt) | 2836 (wt) | 7681 (wt) | 2108 (wt) | 9066 (wt) |
| L. fermentum (DSM 32130) | 3 | 3 | 3 | 0 | 0 | 1 |
| L. gasseri (NCIMB 11718) | 3 | 2 | 3 | 1 | 0 | 1 |
| L. salivarius (NCIMB 8816) | 3 | 3 | 3 | 3 | 3 | 3 |
| Aggregation category | 1 | 2 | 3 | 4 | 5 | |
| Aggregation index | <20% | 20-40% | 41-60% | 61-80% | >80% | |
| | ATCC 33277$^T$ | 1807 (wt) | 2836 (wt) | 7681 (wt) | 2108 (wt) | 9066 (wt) |
| L. fermentum (DSM 32130) | 5 | 4 | 4 | 2 | 1 | 2 |
| L. gasseri (NCIMB 11718) | 5 | 4 | 4 | 3 | 1 | 2 |
| L. salivarius (NCIMB 8816) | 5 | 5 | 5 | 5 | 4 | 5 |

EXAMPLE 3: INHIBITORY ACTIVITY OF PROBIOTIC STRAINS AGAINST DISEASE-ASSOCIATED BACTERIA

The inhibitory activity of selected probiotic strains, inter alia L. salivarius NS 13, against peridontitis-associated oral bacterial species (indicator strains) was determined. The indicator strains were:

Porphyromonas gingivalis ATCC 33277
Porphyromonas endodontalis ATCC 35406
Tannerella forsythia ATCC 43037
Filifactor alocis ATCC 35896
Eubacterium saphenum ATCC 49989
Parvimonas micra ATCC 33270
Lachnoanaerobaculum saburreum ATCC 33271

A delayed antagonism method was performed in triplicate. The test strains were grown on blood agar as streak for 24 or 48 h and then killed by exposure to chloroform. Indicator strains were cross-streaked and incubated for up to 72 h.

L. Salivarius NS 13 had activity against multiple indicator strains as shown in table 4:

TABLE 4

| | Lactobacillus salivarius NS 13 |
|---|---|
| Porphyromonas gingivalis ATCC 33277 | — |
| Porphyromonas endodontalis ATCC 35406 | — |
| Tannerella forsythia ATCC 43037 | — |
| Fillfactor alocis ATCC 35896 | + |
| Eubacterium saphenum ATCC 49989 | + |
| Parvimonas micra ATCC 33270 | + |
| Lachnoanaerobaculum saburreum ATCC 33271 | — |

EXAMPLE 4: PROBIOTIC LOZENGE OR COMPRIMATE

| | | | Isomalt Comprimates | | |
|---|---|---|---|---|---|
| No | Block | Ingredients | Placebo | Probiotic only | +Flavor |
| 1 | A | Magnesium Stearate | 1.800% | 1.800% | 1.800% |
| 2 | | Acesulfam | 0.050% | 0.050% | 0.050% |
| 3 | | Sucralose | 0.025% | 0.025% | 0.025% |
| 4 | | Probiotic Material | | 1.000% | 1.000% |
| 5 | | Flavor (e.g. 134229 Optamint Peppermints/d) | | | 0.500% |
| 6 | B | Isomalt | 98.125% | 97.125% | 96.625% |
| | | Sum total | 100.00% | 100.00% | 100.00% |

Production Method:

Components 1 and 6 are dried in a vacuum compartment drier at 50° C. and a pressure of max. 10 mbar for 16 hours.

All components are weight out exactly components 1, 2, 3, 4 and 5 combined and thoroughly mixed (block A). The probiotic material is applied in lyophilized form having an activity of about $10^5$ to $10^{12}$ colony forming units (CFU) per gram.

Block A is subsequently added to component 6 and mixed thoroughly for 5 minutes.

The powder mixture is pressed into tablets in a tablet press EKO (Korsch AG, Berlin) at an adjusted pressure of 15-20 kN target parameters:

tablet diameter: 20 mm tablet weight: 2.0 g.

Storage at RT in sealed aluminum sachets. Per 5 lozenges 1 g of desiccant is used for dehumidification (activated by 3 h storage at 105° C. in a vacuum compartment drier).

EXAMPLE 5: POWDER DENTIFRICE

| | | | Toothpowder | | |
|---|---|---|---|---|---|
| No | Block | Ingredients | Placebo | Probiotic only | +Flavor |
| 1 | A | Magnesium Carbonate | 3.00% | 3.00% | 3.00% |
| 2 | | Sodium Bicarbonate | 2.00% | 2.00% | 2.00% |
| 3 | | Sodium Fluoride | 0.25% | 0.25% | 0.25% |
| 4 | | Sodium Saccharin | 0.60% | 0.60% | 0.60% |
| 5 | B | Probiotic Material | | 4.00% | 4.00% |

-continued

| No | Block | Ingredients | Toothpowder Placebo | Probiotic only | +Flavor |
|---|---|---|---|---|---|
| 6 | | Flavor (e.g. 134229 Optamint Peppermint s/d) | | | 2.00% |
| 7 | C | Calcium carbonate | 94.15% | 90.15% | 88.15% |
| | | Sum total | 100.00% | 100.00% | 100.00% |

Production Method:

Component 7 is dried in a vacuum compartment drier at 50° C. and a pressure of max. 10 mbar for 16 hours.

All components are weight out exactly.

Components 1, 2, 3 and 4 are combined and thoroughly mixed together (block A).

Components 5 and 6 are, if necessary, combined and thoroughly mixed (block B). The probiotic material is applied in lyophilized form having an activity of about $10^5$ to $10^{12}$ colony forming units (CFU) per gram.

Blocks A and B are subsequently combined and thoroughly mixed together.

The mixture is added to component 7 and mixed thoroughly for 5 minutes.

The powder mixture is made up into portions of 0.5 g each storage at RT together with 1 g of desiccant per portion (activated by 3 h storage at 105° C. in a vacuum compartment drier) in sealed aluminum sachets.

EXAMPLE 6: POWDER DENTIFRICE

| No | Block | Ingredients | Toothpaste tablets |
|---|---|---|---|
| 1 | A | Magnesium Carbonate | 3.00% |
| 2 | | Sodium Bicarbonate | 2.00% |
| 3 | | Sodium Fluoride | 0.25% |
| 4 | | Sodium Saccharin | 0.60% |
| 5 | | Sodium Laurylsulphate | 0.50% |
| 6 | | Magnesium Stearate | 1.00% |
| 7 | B | Flavor (e.g. 134229 Optamint Peppermint s/d) | 2.00% |
| 8 | | Probiotic Material | 6.67% |
| 9 | C | Calcium Carbonate | 17.00% |
| 10 | | Microcrystalline Cellulose | 66.98% |
| | | Sum total | 100.00% |

Production Method:

Components 6, 9 and 10 are dried in a vacuum compartment drier at 50° C. and a pressure of max. 10 mbar for 16 hours.

All components are weight out exactly.

Components 1, 2, 3, 4, 5 and 6 are combined and thoroughly mixed together (block A).

Components 7 and 8 are combined and thoroughly mixed together (block B). The probiotic material is applied in lyophilized form having an activity of about $10^5$ to $10^{12}$ colony forming units (CFU) per gram.

Blocks A and B are subsequently combined and thoroughly mixed together.

Components 9 and 10 are combined and thoroughly mixed together (block C).

The two mixtures (Block NB and Block C) are combined and mixed thoroughly for 5 minutes.

The powder mixture is pressed into tablets in a tablet press EKO (Korsch AG, Berlin) at an adjusted pressure of 15-20 kN target parameters tablet diameter: 9 mm tablet weight: 0.3 g Storage at RT in sealed aluminum sachets. Per 3 tablets 1 g of desiccant is used for dehumidification (activated by 3 h storage at 105° C. in a vacuum compartment drier).

EXAMPLE 7: CHEWING GUM

| No | Ingredients | Chewing gum with Vegetable Oil, Probiotics in Flavor | | Chewing gum with Vegetable Oil, Probiotics in Oil | |
|---|---|---|---|---|---|
| 1 | Gum Base (e.g. Geminis T) | 30.00% | Block A | 30.00% | Block A |
| 2 | Isomalt (here: Isomalt ST-PF) | 65.00% | Block B | 65.00% | Block B |
| 3 | Sucralose coated (10% in wax) | 1.00% | | 1.00% | |
| 4 | Deoiled Soy Lecithin (here: Emulbur IP) | 0.30% | | 0.30% | |
| 5 | Vegetable Oil - Triglyceride | 1.60% | Block C | 1.60% | Block C |
| 6 | Probiotic Material | 0.80% | Block D | 0.80% | |
| 7 | Flavor (e.g. 203191 Optamint Peppermint) | 1.30% | | 1.30% | Block D |

Production Method:

Component 2 is dried in a vacuum compartment drier at 50° C. and a pressure of max. 10 mbar for 16 hours.

All components are weight out exactly.

Component 1 is tempered to 45-59° C. in a chewing gum lab-kneader with the heating kneaded until a homogenous mass is obtained. The heating is on during the whole mixing process.

Components 2, 3 and 4 are added subsequently and kneaded until the mixture is homogenous and no powder is visible anymore.

According to the formula component 6 is either worked into component 5 (block C) or component 7 (block D). The probiotic material is applied in lyophilized form having an activity of about $10^5$ to $10^{12}$ colony forming units (CFU) per gram. The components are mixed until an even suspension is obtained.

First, block C is added to the chewing gum mass and kneaded again until a homogenous mass is obtained.

Last, block D is processed accordingly. After addition the composition has to be kneaded until an even chewing gum mass is obtained.

The mass is taken out of the mixer and is formed into mini-sticks by an embossing roller using the embossing set "slabs".

Storage at RT in sealed aluminum sachets. Per 7 chewing gums 1 g of desiccant is used for dehumidification (activated by 3 h storage at 105° C. in a vacuum compartment drier).

EXAMPLE 8: PROBIOTIC BEADLETS

| components | probiotic beadlets diets with low load, without aroma, with dye, with gellan gum wt. % | probiotic beadlets with low load, with aroma, with dye, with gellan gum wt. % | probiotic beadlets with high load, without aroma, without dye, without gellan gum, high water content wt. % | probiotic beadlets with high load, without aroma, without dye, without gellan gum, low water content wt. % |
|---|---|---|---|---|
| Alginate | 1.75 | 1.65 | 1.44 | 1.57 |
| Gum arabic | 1.25 | 1.18 | 0.60 | 0.65 |
| Wheat fiber | 1.125 | 1.06 | 0.52 | 0.57 |
| Dye | 0.0125 | 0.018 | — | — |
| Aroma | — | 1.41 | — | — |
| Glycerol | 0.1875 | — | — | — |
| probiotic | 1.125 | 1.35 | 7.20 | 7.83 |
| Gallon Gum | 0.0625 | 0.059 | — | — |
| Water | Add to 100 | Add to 100 | Add to 100 | Add to 100 |
| load | approx. 20% | approx. 20% | approx. 74% | approx. 74% |

Production Method:

Production of the calcium chloride bath for precipitation of the alginate beadlets:

A 2% calcium chloride solution is produced from distilled water and calcium chloride. Care has to be taken that the CaCl$_2$ is completely dissolved.

Production of the alginate solution (instead of alginate also pectin or gellan gum may be used):

In a reaction vessel with a stirrer and which is suitable to the batch size, water is provided.

The stirrer is turned on and, while stirring at a high level, the respective amounts of alginate, gum *arabicum*, wheat fiber and probiotic, as well as the optionally required gellan gum are added.

The mixture is heated to 80° C. while stirring and kept at this temperature for 5 minutes—during this step the gel forming components are dissolved.

Afterwards, the heating is turned off and the hot gel solution is further stirred for at least 30 minutes until it is free of lumps.

Subsequently, the solution is cooled by refrigeration to 39-43° C. while stirring.

In a further vessel, the aroma and the dye are provided if required and thoroughly mixed In case no aroma is used, the dye is mixed with glycerol.

When the dye dispersion is mixed homogenously, it is added to the batch vessel with the alginate solution. The mixing vessel is washed several times with approx. 10% of the amount of alginate solution used of water and added to the dispersion.

The alginate dispersion is stirred further for at least 5 minutes.

Subsequently, the batch is stirred for further at least 15 minutes at a low speed to remove potentially present air.

Dripping of the Alginate Solution into the Calcium Chloride Solution for Precipitation of the Beadlets:

The alginate dispersion is moved to a tightly sealable pressure stable reaction vessel having two outlets. At one outlet pressurized air is applied. The second outlet leads to the nozzles of the dripping unit via a tube.

The reaction vessel is tempered over a heating plate so that the alginate solution reaches a temperature of approx. 45° C. The solution is slightly stirred with a magnet stirrer.

After application of pressure to the reaction vessel, alginate solution is pressed towards the nozzles, which are set to oscillation by an oscillator. By adaption of pressure and the frequency of the oscillator, the size of the resulting drops at the tips of nozzles may be adjusted.

The drops of alginate solution forming at the tips of the nozzles fall into a collection vessel in the form of a funnel in which the calcium chloride solution prepared at the beginning circulates.

The cured alginate beadlets pass with the calcium chloride solution through the funnel and are collected in a sieve, the collected calcium chloride solution is pumped back into the funnel below the dripping unit and thus recycled.

The beadlets are dried in an Aeromatic flowbed-drier at an supply air temperature of 80° C. until an exhaust air temperature of 45° C. is reached.

The invention claimed is:

1. A method for treating gingivitis and/or periodontitis comprising orally administering to a subject a microorganism or a mixture of two or more microorganisms selected from the group consisting of *Lactobacillus delbrueckii* subsp. *lactis* LL-G41 (CCTCC M 2016652), *Lactobacillus fermentum* 35D (DSM 32130), *Lactobacillus gasseri* NS8 (NCIMB 11718), *Lactobacillus salivarius* NS 12 (NCIMB 8816), *Streptococcus salivarius* NS18 (CBS 142430), and *Streptococcus salivarius* NS19 (CBS 142431).

2. The method of claim 1, wherein the microorganism or the mixture of two or more microorganisms is (an) attenuated or (a) dead microorganism(s).

3. The method of claim 1, wherein the microorganism or the mixture of two or more microorganisms has an inhibitory activity on the growth of one or more disease-associated microorganisms selected from the group consisting of *Porphyromonas gingivalis, Porphyromonas endodontalis, Tannerella forsythia, Filifactor alocis, Eubacterium saphenum, Parvimonas micra*, and *Lachnoanaerobaculum saburreum*, and wherein the microorganism is *Lactobacillus salivarius* NS12 (NCIMB 8816).

4. The method of claim 1, wherein the microorganism or the mixture of two or more microorganisms is additionally capable of treating inflammation in an oral cavity by inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB, and wherein the microorganism or the mixture of two or more microorganisms is/are selected from the group consisting of *Lactobacillus delbrueckii* subsp. *lactis* LL-G41 (CCTCC M 2016652), *Lactobacillus fermentum* 35D (DSM 32130), and *Lactobacillus salivarius* NS1.2 (NCIMB 8816).

5. The method of claim 1, wherein the microorganism or the mixture of two or more microorganisms forms co-aggregates with oral bacterial species selected from the group consisting of *Porphyromonas gingivalis, Porphyromonas endodontalis, Tannerella forsythia, Filifactor alocis* and *Eubacterium saphenum*.

6. The method of claim 1, wherein the microorganism or the mixture of two or more microorganisms is orally administered to the subject in an oral composition, wherein the microorganism or the mixture of two or more microorganisms is present in the oral composition in a range from 0.01 to 100%, with respect to the total weight of the oral composition, and/or wherein the total amount of the microorganism or the mixture of two or more microorganisms is in the range from $1\times10^3$ to $1\times10^{11}$ colony forming units (CFU).

7. The method of claim 6, wherein the oral composition is selected from the group consisting of a toothpaste, a tooth gel, a tooth powder, a tooth cleaning liquid, a tooth cleaning foam, a mouth wash, a mouth spray, dental floss, a chewing gum, and a lozenge.

\* \* \* \* \*